United States Patent [19]

Schiffman et al.

[11] Patent Number: 4,928,707

[45] Date of Patent: May 29, 1990

[54] ELECTRONIC PRESSURE ALGOMETER APPARATUS

[75] Inventors: Eric L. Schiffman; James R. Fricton, both of Minneapolis; Lawrence M. Espy, Edin, all of Minn.

[73] Assignee: Regents of the University of Minnesota, St. Paul, Minn.

[21] Appl. No.: 241,112

[22] Filed: Sep. 2, 1988

Related U.S. Application Data

[63] Continuation-in-part of Ser. No. 26,625, Mar. 17, 1987, Pat. No. 4,768,521.

[51] Int. Cl.$^5$ .............................................. A61B 5/10
[52] U.S. Cl. ...................................... 128/774; 73/81
[58] Field of Search ...................... 128/744, 774–782; 73/1 B, 81, 82, 85

[56] References Cited

U.S. PATENT DOCUMENTS

| | | | |
|---|---|---|---|
| 3,156,237 | 11/1964 | Edmark | 128/774 |
| 3,782,365 | 1/1974 | Pinna | 73/81 |
| 4,122,837 | 10/1978 | Leonard | 128/774 |
| 4,132,224 | 1/1979 | Randolph | 128/774 |
| 4,159,640 | 7/1979 | Lévêque et al. | 128/774 |
| 4,249,417 | 2/1981 | Feldstein et al. | 128/774 |
| 4,250,894 | 2/1981 | Frei et al. | 128/774 |
| 4,337,780 | 7/1982 | Metrick | 128/774 |
| 4,338,950 | 7/1982 | Barlow, Jr. et al. | 128/687 |
| 4,635,506 | 3/1987 | Romanovskaya | 128/677 |
| 4,641,661 | 2/1987 | Kalarickal | 128/774 |

FOREIGN PATENT DOCUMENTS

| | | | |
|---|---|---|---|
| 0637637 | 12/1978 | U.S.S.R. | 73/81 |
| 0665245 | 5/1979 | U.S.S.R. | 73/81 |
| 1185443 | 3/1970 | United Kingdom | |

OTHER PUBLICATIONS

"Pain and Soft Tissue Pathology Instruments", from Pain Diagnostics & Thermography, Great Neck, New York, four-page brochure, Bulletin 8401.

Primary Examiner—Max Hindenburg
Attorney, Agent, or Firm—Merchant, Gould, Smith, Edell, Welter & Schmidt

[57] ABSTRACT

A pressure algometer apparatus (50, 100) is provided. The pressure algometer apparatus (50, 100) provides a combination mechanical and electrical pressure algometer including a hand held pressure transducer (52, 102) electrically interconnected (53, 138) to an amplifier meter arrangement (54, 104). The algometer apparatus (50, 100) includes a pressure readout display (70, 144) which indicates the pressure sensed by the pressure transducer (52, 102). A recording device (150) may be attached to the algometer apparatus (100) to provide a permanent record (148) of the pressure sensed by the pressure transducer (102). The pressure algometer apparatus (100) further includes a latch device (106) which, when activated, holds the pressure readout display (144) constant and marks the permanent record (148).

21 Claims, 3 Drawing Sheets

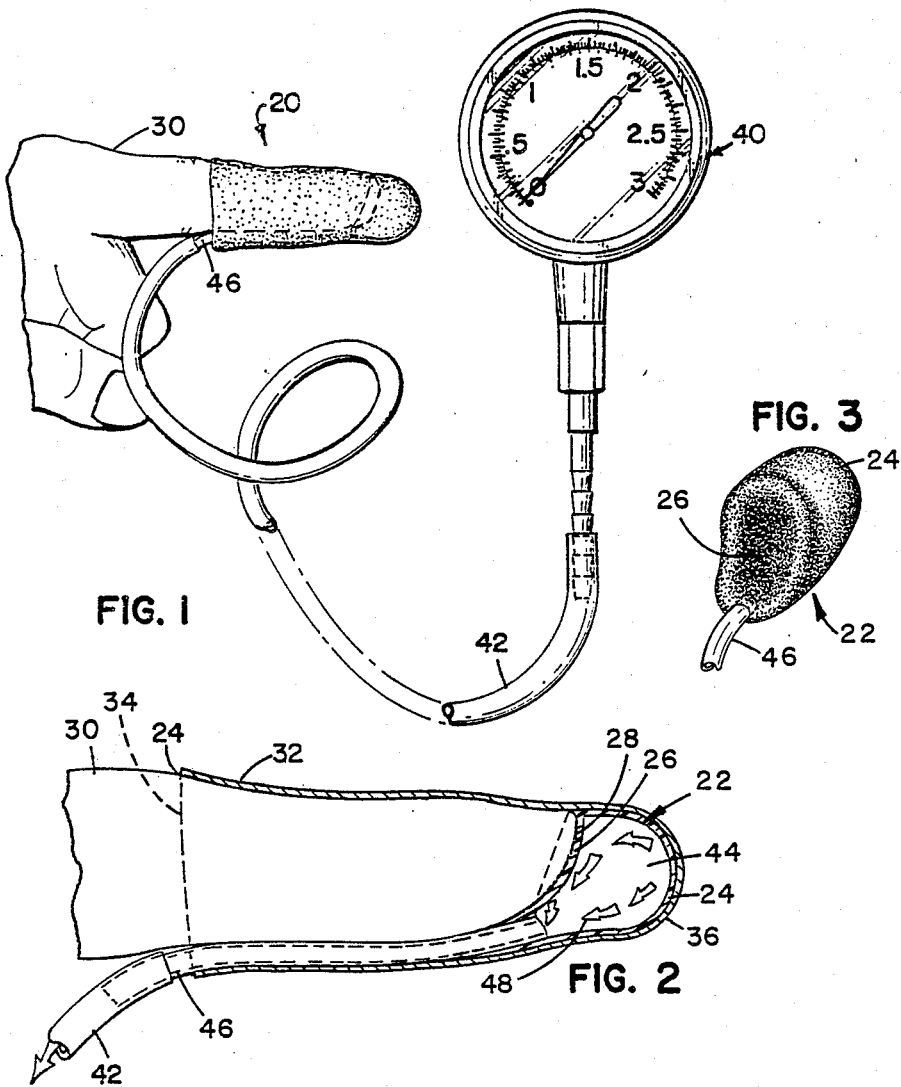
FIG. 1
FIG. 2
FIG. 3
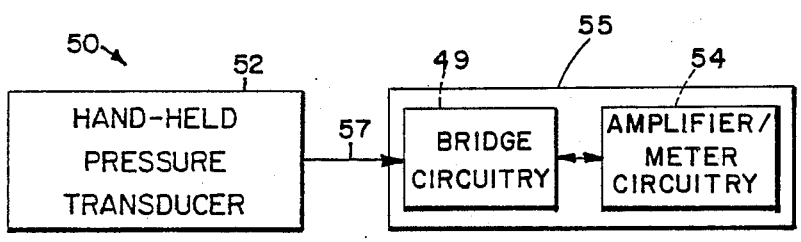
FIG. 4

ELECTRONIC PRESSURE ALGOMETER APPARATUS

The government has rights in this invention pursuant to Contract No. 1R03DE07413-01 awarded by the N.I.D.R.

This is a continuation-in-part of Ser. No. 026,625, filed on Mar. 17, 1987, Pat. No. 4,768,521.

BACKGROUND OF THE INVENTION

The present invention relates to a pressure algometer apparatus, and more particularly, to a pressure algometer apparatus for diagnosis of muscle pain or tenderness when subjected to pressure.

Myofascial pain and dysfunction is the most common disorder causing chronic head and neck pain. Traditionally, diagnosis and assessment of the severity of this disorder depends o the tenderness of myofascial tissue at specific locations, often referred to as trigger points, to manual palpation. Manual palpation is accomplished by using one's fingers to apply varying pressure against the trigger points and to observe patient response. However, this technique is often unreliable, due in part to the inability to accurately measure the variation in pressure applied at the trigger point. The present invention solves this and other problems associated with diagnostic technique.

U.S. Pat. No. 4,337,780 issued to Metrick shows that pressure sensing devices have been used to test muscle strength. The Metrick patent teaches the use of an air tight bag of any suitable configuration depending on the muscle whose strength is to be tested, which is interconnected by tubing to a pressure responsive device so as to form an air tight compartment. The pressure responsive device consists of any suitable device commercially available to measure air pressure, such as a sphygmomanometer. In use, the air tight bag is typically attached to the palm side surface of the distal end of the tester's index finger by an elastic band or the like and/or is attached to the back of the tester's hand.

The Metrick invention is used to test muscle strength and not muscle pain threshold or tenderness. Muscle strength testing devices have long been used. In muscle strength testing, the force applied to the overall muscle is measured. The configuration and consistency of the device used to apply the force is not critical. Therefore, in addition to other differences, there is no teaching or suggestion in Metrick of a pressure sensitive device having a specific configuration and consistency for testing muscle trigger points.

As indicated in a brochure entitled, "Pain and Soft Tissue Pathology Instruments", Pain Diagnostics and Thermography of Great Neck, N.Y. appears to be marketing what are referred to as pain and soft tissue pathology instruments. These instruments apparently utilize a structural column arrangement, possibly a spring biased plunger arrangement, which interconnects a probe end of the instrument to a pressure gauge. In use, the user places the probe end against the tissue to be tested and applies pressure by grasping the gauge housing and forcing the gauge housing toward the probe end, whereupon the pressure is indicated at the pressure gauge. The instrument does not include a pressure probe adapted for positioning at the end of a user's finger and, as a result, does not offer the small size and flexibility of a user's finger in getting at hard to reach places, such as the underside of one's jaw. The pressure gauge is also rigidly attached to the pressure probe which further reduces the flexibility of the instrument.

The present invention solves many of the problems associated with existing algometer devices.

SUMMARY OF THE INVENTION

The present invention relates to a pressure algometer apparatus. The algometer apparatus includes pressure sensitive probe means for use in applying pressure to localized sites and for sensing the pressure applied to the localized sites. The pressure probe means includes hollow elastic housing means including surface means proximate a first end for receiving a distal end of a user's finger, the housing means including proximate a second end body tissue engaging surface means. Pressure responsive means is present for indicting pressure variations sensed by pressure sensitive probe means. Interconnection means interconnects an interior of the elastic housing means to the pressure responsive means for providing air communication between the interior of the elastic housing means and the pressure responsive means.

The present invention also relates to an embodiment of the pressure algometer apparatus which includes transducer means for providing an electrical output signal indicative of the pressure sensed. This pressure responsive means is electrically interconnected to the pressure sensitive probe means for receiving the electrical output signal from the pressure sensitive probe means. The pressure responsive means includes readout means for indicating the pressure sensed by the pressure sensitive means. Means is further provided for electrical interconnection of the pressure algometer apparatus to a source of electrical energy.

The present invention further relates to an embodiment of the pressure algometer apparatus which includes pressure responsive means for providing an electrical output signal indicative of the pressure sensed. The pressure responsive means further includes digital readout means for indicating the pressure sensed by the pressure algometer apparatus. The pressure responsive means is electrically interconnected to a pressure sensitive probe means such that the pressure responsive means receives electrical signals from the pressure sensitive probe means indicative of the pressure sensed. The pressure responsive means further is electrically interconnected to a latch means for providing an output signal which selectively holds the digital readout means output constant for intervals of time. Optionally, a pressure responsive means further is electrically interconnected to a recording means for providing a permanent record of pressure sensed by the probe means. The recording means further includes means for receiving an output signal from the latch means which indicates the operational state of the latch and means for indicating the operational state on the permanent record. The pressure responsive means is further electrically interconnected to a source of electrical energy.

The present invention further relates to a method for diagnosing muscle tissue pain and dysfunction. The method includes the steps of manually palpating muscle tissue trigger points using pressure sensitive means inserted over a user's finger and forming an air tight seal therewith, the pressure sensitive means being interconnected to, and in air communication with, pressure responsive means for indicating variations in pressure. The method includes a second step of observing the pressure indicated at the pressure responsive means and observing the patient's response to such pressure.

In the preferred method, the patient will be asked to indicate when they first start feeling pain as opposed to pressure. The user will then gradually increase the amount of pressure applied until the patient indicates they feel pain as opposed to only pressure. The user will typically observe the patient for any outward signs of pain; e.g., flinch, expression, etc.

In one embodiment, the present invention provides an all mechanical pressure algometer apparatus which is easy to use and yet relatively accurate. In addition, the invention provides a pressure algometer apparatus which is relatively inexpensive. The pressure algometer apparatus will, therefore, be an efficient screening device for use in this field. This embodiment also has many other advantages. First, the shape and firmness of the pressure sensitive probe means of the pressure algometer is such that it effectively serves as an extension of one's finger. The relatively small size and flexibility of a user's finger also make the invention particularly useful for getting at hard to reach places such as the underside of one's jaw. Moreover, The pressure sensitive probe portion of the pressure algometer is deformable as to conform to the surface of the tissue being tested. The soft, deformable nature of the probe portion also reduces the likelihood that the probe portion itself will induce additional pain. Finally, the probe portion of the mechanical algometer is preferably covered by and retained at the distal end of the user's finger by a throw away retainer member such as a finger cot. This makes use of the pressure algometer of the present invention extremely sanitary. However, the numbers obtained through the mechanical algometer are expressed in pound per square inch (PSI). Since these numbers are relative due to the variable geometry of the individual finger, absolute calibration is difficult.

In an alternative embodiment of the invention, the apparatus can be absolutely calibrated because it employs a tissue engaging surface of constant geometry and relies on an electronic transducer, as opposed to air or gas pressure. The version of the invention may be somewhat more expensive and due to its increased accuracy, will probably be used mostly in a clinic setting. In the embodiments of this invention wherein a portable battery supply is provided, the device will be readily portable.

In another alternative embodiment of the invention, a digital readout is provided for easy readout and improved accuracy. The alternative embodiment further comprises power supply inputs capable of deriving power from A.C. voltage supplies like those commonly found in a clinical setting.

These and various other advantages and features of novelty which characterize the present invention are pointed out with particularity in the claims annexed hereto and forming a part hereof. However, for a better understanding of the invention, its advantages and objects attained by its use, reference should be made to the drawings, which form a further part hereof, and to the accompanying descriptive matter, in which there is illustrated and described a preferred embodiment of the invention.

BRIEF DESCRIPTION OF THE DRAWINGS

In the drawings, in which like reference numerals indicate corresponding parts throughout, FIG. 1 is a perspective view of one embodiment of a pressure algometer positioned at the distal end of a user's finger by use of finger cot in accordance with the principles of the present invention;

FIG. 2 is an enlarged partial cross-sectional view of the embodiment shown in FIG. 1;

FIG. 3 is a perspective view of one embodiment of a pressure sensitive probe member in accordance with the principles of the present invention;

FIG. 4 is a block diagram of a second embodiment of a pressure algometer apparatus in accordance with the principles of the present invention;

DETAILED DESCRIPTION OF A PREFERRED EMBODIMENT

Figure 6:
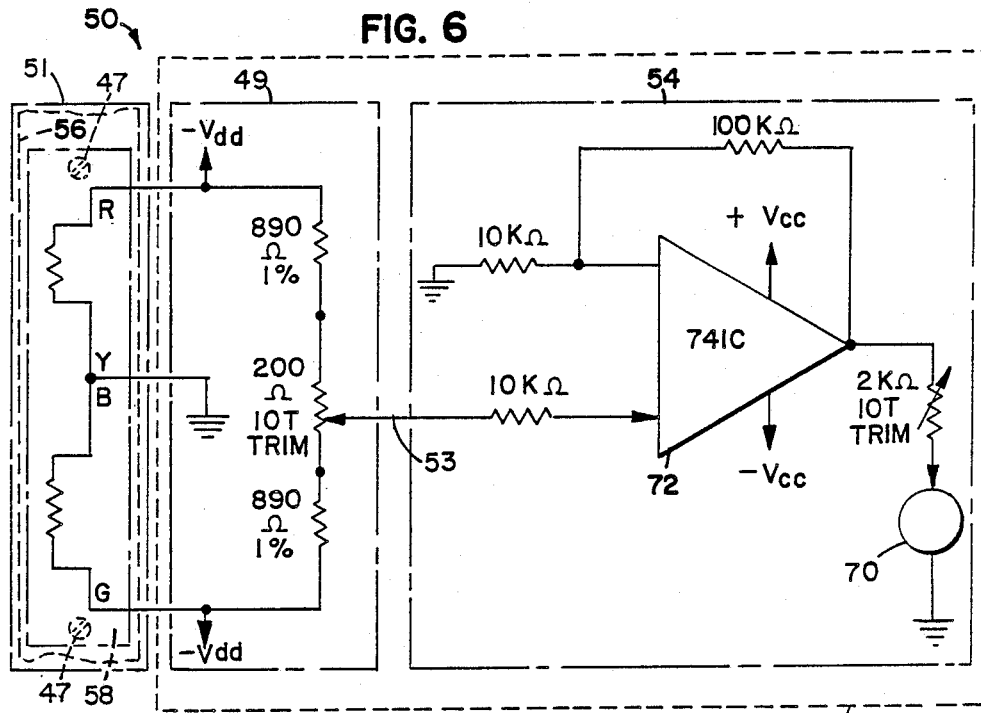
FIG. 6 is a schematic of the embodiment shown in FIG. 5.
Figure 7:
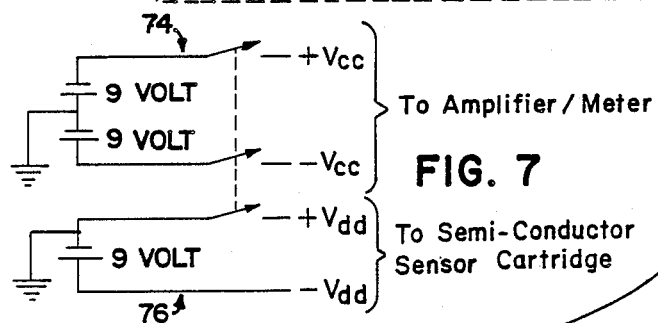
FIG. 7 is a schematic of one embodiment of a possible power supply for the embodiments shown in FIGS. 4 through 6.

Illustrated in FIGS. 1 through 3, is an embodiment of an algometer apparatus, generally referred to by the reference number 20, in accordance with the principles of the present invention. In the embodiment shown, the algometer apparatus 20 includes a resilient deformable, one-piece, integrally molded, plastic bladder member which functions as a pressure sensitive probe member 22. The pressure sensitive probe member is deformable but maintains its shape when not under pressure. The probe member has a first end surface providing a muscle tissue engaging surface 24 similar to a distal end of a user's finger and a second end surface providing a finger engaging surface 26 being configured and contoured for receiving a distal end surface 28 of a user's finger. In the embodiment shown, the surface 26 has a generally concave shape inversely similar to the distal end surface 28 of a user's finger for receiving the user's finger such that the user's finger uniformly abuts the surface 26 when pressure is applied. The balloon-like probe member 22 is configured to closely approximate and standardize the surface area, shape and firmness of a distal end portion of an index finger. The probe member 22 is interconnected to a 0 to 3 pound per square inch (PSI) low pressure diaphragm gauge by a length of vinyl tubing 42. As illustrated, the tubing 42 is interconnected to an interior area (cavity) 44 of the probe member 22 by a metal section of tubing 46.

In use, the probe member 22 is preferably retained at the distal end portion 28 of the user's finger 30 by a flexible tubular piece of material 32, such as a finger cot or the like, open at one end 34 for insertion of the user's finger 30 and closed at the other end 36.

As illustrated by the arrows 48, when the distal end portion 28 of the user's finger 30 is forced against the end surface 26 of the probe member 22, air as generally illustrated by the arrows 48, is forced into the tubing 46 as the probe member 22 deforms and the interior area 44 decreases. The pressure responsive, low pressure diaphragm gauge 40 then provides a readout of the pressure variations created in the interior area 44 of the probe member 22. The probe member 22 is preferably configured such that user's finger 30 does not hit the end surface 24 when pressure within normal operating ranges is applied.

In the preferred embodiment, the probe member 22 is made by dipping an aluminum mold in Tasco Vinyl Dispersion Number 60 Plastisol. After curing, the mold is removed by cutting the bladder member 22, and then resealing with cyclohexanone solvent.

In use, a user positions the probe member 22 at the distal end surface 28 of the index finger 30 and then inserts the index finger 30 into the tubular material 32 so as to facilitate retention of the probe member 22 proximate the distal end surface 28 of the index finger 30. A user then manually palpates muscle tissue trigger points using the probe member 22 which functions as a pressure sensitive device. The user typically will proceed by applying sufficient pressure against a muscle trigger point by forcing the index finger 30 against the end surface 26 of the probe member 22 such that the patient can sense the pressure but normally will not sense any pain. The user then gradually increases the amount of pressure applied until the patient reports feeling even the slightest pain. The user then observes the pressure readout indicated at the low pressure diaphragm gauge which serves as a pressure responsive device. This is then recorded as the pain threshold. If no pain threshold is elicited from the patient, the top end of the pressure gauge scale reading, roughly 1.0 pounds per inch, is recorded. After a predetermined interval; e.g., 5 seconds, the process might be repeated at the same trigger point. This process is repeated at other trigger points as desired. The same patient might then be so evaluated by a second user after a predetermined time; e.g., 5 minutes, so as to provide comparison results. It will be appreciated that the specific pressure utilized will vary.

Typically, the readout obtained is expressed in PSI and is relative, since the variable geometry of the user's finger makes absolute calibration difficult. As previously discussed, however, the present invention is particularly useful for getting at hard to reach places and is relatively inexpensive and entirely mechanical, so as to serve as a good screening device for field use as well as in the hospital facility. It will be appreciated that the present invention has numerous applications other than diagnosis of muscle pain or tenderness; e.g., diagnosis of joint capsulization, tissue compliance, sports medicine applications, etc.

Figure 5:
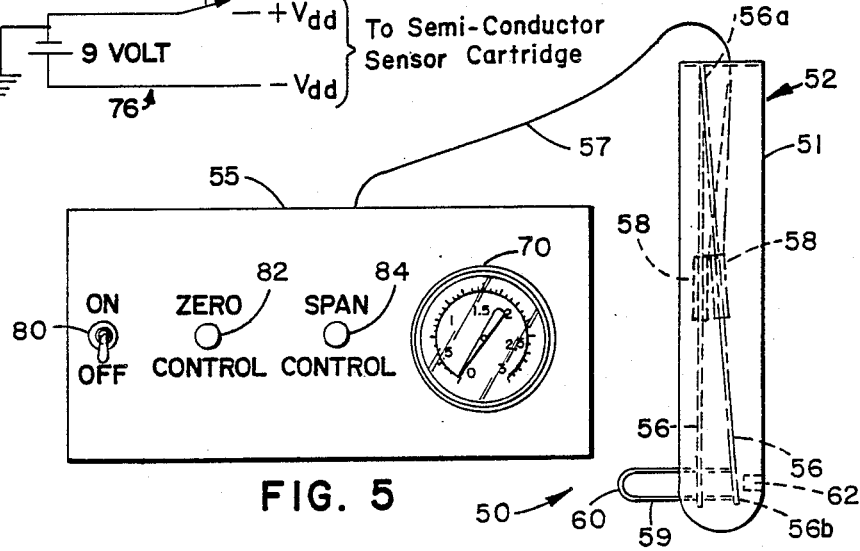
FIG. 5 is a perspective view of the embodiment shown in FIG. 4.

Illustrated in FIGS. 4-7 is an alternative embodiment of an algometer apparatus, generally referred to by the reference numeral 50, in accordance with the principles of the present invention. The algometer apparatus 50 shown comprises a hand held pressure transducer device 52, supporting bridge electronics 49 for receiving electrical input signals from the hand held pressure transducer device 52, and an amplifier/meter circuitry arrangement 54 electrically interconnected to the bridge electronics 49 by a suitable electrical interconnection 53. The supporting bridge electronics 49 and the amplifier/meter circuitry 54 are disposed in a housing 55. The transducer 52 includes a stainless steel bar 56 mounted in a housing 51. A Kistler/Morse semiconductor strain gauge sensor cartridge 58 is mounted on the stainless bar 56 by suitable fasteners such as threaded screws 47 so as to sense any deflections of the bar 56. The supporting bridge electronics 49 located in housing 55 are electrically interconnected to the strain gauge sensor cartridge 58 by an electrical cord 57. The two resistors of the semiconductor strain gauge sensor cartridge 58 and the two resistors of the supporting bridge electronics 49 cooperate to provide a bridge function. The electrical interconnection 53 is slidably interconnected to a ten turn (10t) trim resistor so as to enable balancing of the bridge when in a neutral or unstressed state. When the bar 56 is displaced from its neutral state, the bridge function will become unbalanced and a corresponding signal value will be sent to the amplifier/meter circuitry 54 which in turn will output a corresponding signal to the meter 70, causing movement of the meter's pointer. As illustrated in FIG. 5, the steel bar 56 is mounted in the housing 51 so as to be secured against movement at a first end 56a and yet have a free end 56b. Interconnected to the steel bar 56 proximate the free end 56b is a plastic, lightweight, cylindrical probe member 59 oriented at 90° with respect to the housing 51. The probe member 59 is preferably lightweight such that the algometer readout is not affected by orientation of the housing 51. The probe member 59 has a contoured, curved end surface 60 for engaging the localized area of the patient being tested. The user grasps the housing 51 and forces the end surface 60 of the probe member 59 against the muscle trigger point being tested. As the user applies force, the probe member 59 displaces the free end 56b of the steel rod 56. The semiconductor strain gauge sensor 58 then senses this displacement and a corresponding signal is transmitted via the electrical cord 57 to the bridge electronics 49 and then to the amplifier/meter circuitry 54 ultimately resulting in a corresponding readout at the meter 70. A stop or movement limiter 62 might be provided for limiting movement of the steel rod member 56. The sensitivity of the semiconductor sensor cartridge 58 is such that it can detect extremely small deflections of the stainless bar 56 many times under the elastic limits of the stainless steel bar. The amplifier/meter arrangement 54 includes a one-milliampere meter 70 as a pressure indicator device which is driven by an operation amplifier 72. Both the pressure transducer arrangement 52 and its supporting bridge electronics 49, as well as the amplifier/meter arrangement 54 are battery powered, making for a readily portable, easy to use pressure measuring device. Illustrated in FIG. 7, a dual battery arrangement 74 is used to power the amplifier/meter arrangement while a separate battery arrangement 76 is used for the energy supply of the semiconductor sensor cartridge 58 and its supporting bridge electronics 49. In the preferred embodiment, the batteries are also located in the housing 55. The housing 55 is shown further including an on/off switch 80, a meter zero control 82, a meter span control 84, and the meter 70.

A miniature load cell might be used for the transducer so as to provide a more linear output. However, it is anticipated that such an approach would result in a much greater cost. It will be appreciated that numerous types of strain gauge devices might be utilized in keeping with the principles of the invention.

This embodiment can be absolutely calibrated because the probe member 59 muscle tissue engaging surface is of substantially constant geometry. Moreover, it is electronic and relies on a transducer to sense the pressure applied. This embodiment, although somewhat more expensive, is more accurate and will probably be used mostly in a clinical setting.

Figure 8:
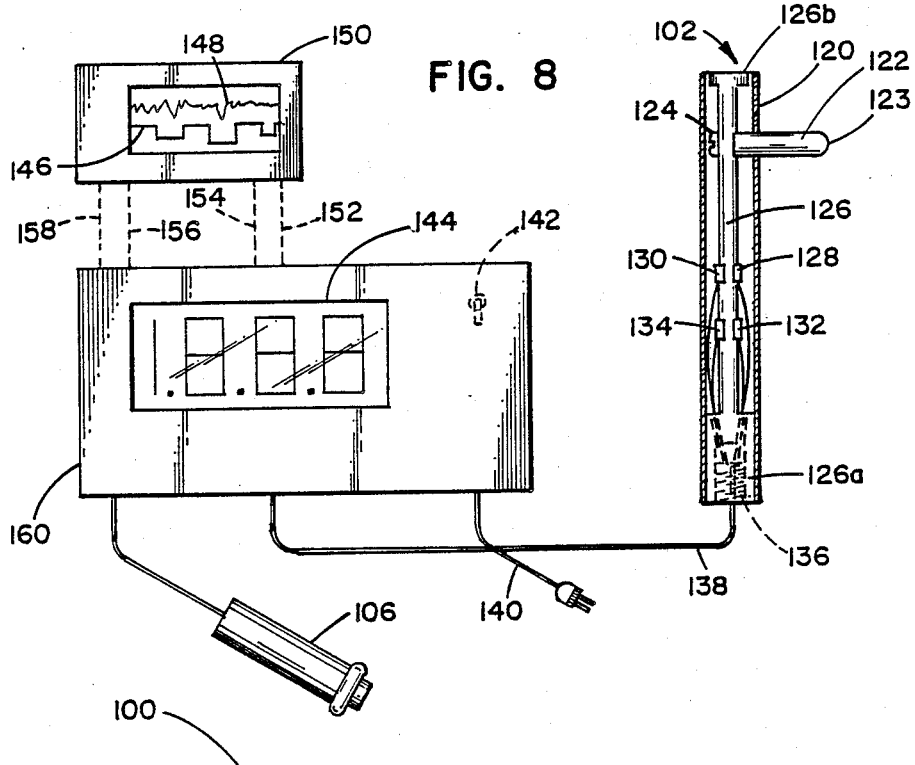
FIG. 8 is a perspective view of a third embodiment of a pressure algometer apparatus in accordance with the principles of the present invention.
Figure 9:
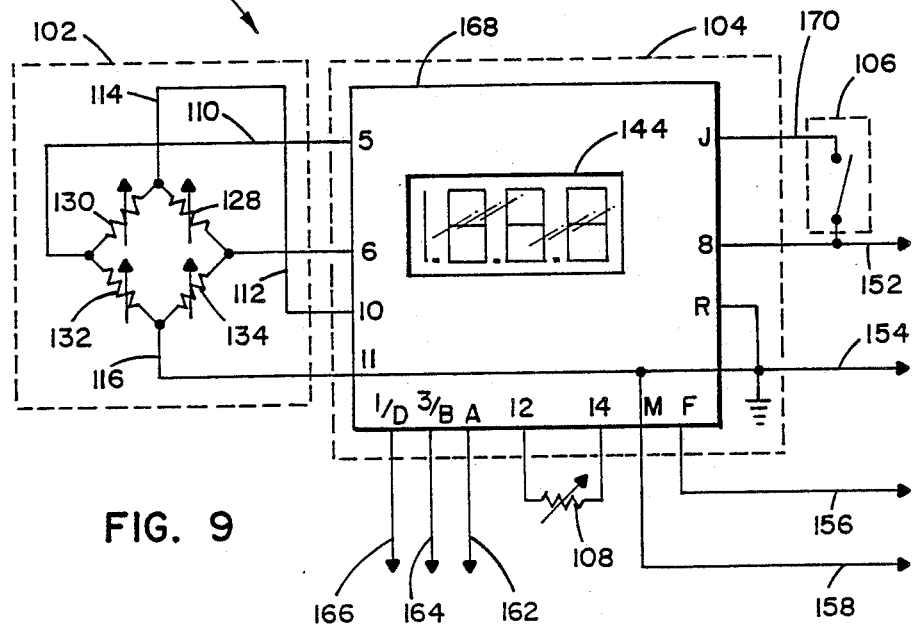
FIG. 9 is a schematic of the embodiment shown in FIG. 8.

Illustrated in FIGS. 8-9 is another alternative embodiment of an algometer apparatus, generally referred to by the reference numeral 100, in accordance with the principles of the present invention. The algometer apparatus 100 shown comprises a hand held pressure transducer device 102, amplifier/meter circuitry 104, latch means 106 and gain adjust means 108. Amplifier/meter circuitry 104 and gain adjust means 108 are disposed in a housing 160.

A transducer device 102 includes an aluminum bar 126 mounted in an aluminum tube housing 120. Kistler/-Morse semiconductor strain gauge sensors 128, 130, 132 and 134 are mounted on aluminum bar 126 by a suitable adhesive. The particular adhesive should be chosen so that it meets temperature conditions and shrinkage constraints for the particular operating environment. The strain gauge sensors can sense any deflections of aluminum bar 126. Strain gauge sensors 128, 130, 132 and 134 cooperate to provide a balanced bridge function. Probe side strain gauge sensors 128 and 132 are interconnected in the bridge such that they are on opposite sides of the bridge. Similarly, strain gauge sensors 130 and 134 are interconnected in the bridge such that they are on opposite sides of the bridge. The particular arrangement of the strain gauge sensors was found to provide the most precise pressure measurements. When aluminum bar 126 is displaced from its neutral state, the bridge function will become unbalanced and a corresponding signal value will be sent to amplifier/meter circuitry 104 through electrical couple 138. Electrical couple 138 comprises electrical interconnections 110, 112, 114 and 116. Amplifier/meter circuitry 104 will respond to the signals received from transducer 102 by outputting a pressure measurement signal to digital meter 144. A corresponding digital readout will appear on digital meter 144.

As illustrated in FIG. 8, aluminum bar 126 is mounted in housing 120 so as to be secured against movement at a first end 126 and yet will have a free end 126b. Aluminum bar 126 is forced against housing 120 through pressure applied with fastener 136 at first end 126a. Interconnected to aluminum bar 126 proximate free end 126b is a plastic, lightweight, cylindrical probe member 122 oriented at 90° with respect to housing 120. Probe member 122 preferably is interconnected to aluminum bar 126 with a fastener 124. Probe member 122 preferably is lightweight such that the algometer measurement is not effected by orientation of housing 120. Probe member 122 has a contoured, curved end surface 123 for engaging the localized area of the patient being tested. The user grasps housing 120 and forces end surface 123 of probe member 122 against the muscle trigger point being tested. As the user applies force, probe member 122 displaces free end 126 of aluminum rod 126. Semiconductor strain gauge sensors 128, 130, 132 and 134 sense this displacement and a corresponding signal is transmitted through electrical couple 138 to amplifier./meter circuitry 104 which results in a corresponding readout on signal meter 144. The sensitivity of strain gauge sensor bridge arrangement 128, 130, 132 and 134 is such that it can detect extremely small deflections of aluminum bar 126 many times less than the elastic limits of the aluminum bar.

Amplifier/meter arrangement 104 includes an acculex DP-723 multipurpose voltage input/output panel meter 168. Panel meter 168 comprises a plurality of signal connector pins. Pins 1 and D of panel meter 168 are electrically interconnected to an A.C. powerline neutral pole through electrical interconnection 166. Pins 3 and B are electrically interconnected an A.C. powerline signal pole through electrical interconnection 164. Pin A is electrically interconnected to earth ground through electrical interconnection 162. Pin 10 provides a strain gauge bridge excitation voltage through electrical interconnection 144. Pin 11 provides an internal ground to the strain gauge bridge through electrical connection 116. Pins 5 and 6 receive positive and negative output signals of the strain gauge bridge through electrical interconnection 110 and 112 respectively. Pin J of panel meter 168 provides a 5 volt D.C. signal to latch 106 through electrical interconnection 170. Preferably a patient would hold latch 106 in a hand. The patient would engage latch 106 by pushing a button proximate to one end of latch 106 (i.e. the active operational state) when he/she feels pain from probe member end surface 123 pressing against a test muscle. Closed latch 106 provides a 5 volt D.C. signal to pin 8 through interconnection 152 which holds the readout on digital meter 144 constant for easy viewing. Pins 12 and 14 of panel meter 168 are operatively interconnected to a gain adjust means 108. Gain adjust means 108 comprises a variable resistive element adjusted to a particular resistance which results in a particular gain for panel meter 168. Housing 160 is shown further including an on/off switch 142 for algometer apparatus.

Optionally, a chart recorder couples to amplifier/meter arrangement 104. Interconnection 152 couples the signal from latch 106 to a positive chart recorder mark input. Electrical interconnection 154 provides an internal ground to a negative chart recorder mark input. Pin F provides an output signal of the instrumentation amplifier to a positive chart recorder input through interconnection 156. Pin M is coupled through interconnection 158 to provide an internal ground to a negative chart recorder input. Chart recorder 150 produces a hard copy analog output of the applied pressure. The output comprises a first line 148 indicative of the pressure applied to the muscle tested and a second line 146 indicative of the open or closed state (i.e. the inactive of active operational state) of latch 106.

It is to be understood, however, that even though numerous characteristics and advantages of the invention have been set forth in the foregoing description, together with details of the construction and function of the invention, the disclosure is illustrative only and changes may be made in detail, especially in matters of shape, size and arrangement of parts, within the principles of the invention, to the full extent indicated by the broad general meaning of the terms in which the appended claims are expressed.

What is claimed is:
1. A pressure algometer apparatus, comprising:
   pressure sensitive means sensing pressure applied to a localized site on a patient's body, the pressure sensitive means including transducer means having a muscle engaging surface of constant geometry for providing an electrical output signal indicative of the pressure sensed;
   pressure responsive means electrically interconnected to the pressure sensitive means for receiving the electrical output signal from the pressure sensitive means, the pressure responsive means including readout means for indicating the pressure sensed by the pressure sensitive means;
   coupling means for electrical interconnection of the pressure algometer apparatus to source of electrical energy; and
   flexible structure means for electrically and flexibly interconnecting the pressure sensitive means to the pressure responsive means whereby the pressure sensitive means can be manipulated independently of the pressure responsive means, the pressure responsive means including supporting bridge electronics having a plurality of resistors cooperating with the pressure sensitive means to provide a bridge function, a trim resistor being further provided in the pressure responsive means so as to enable balancing of the bridge electronics when in a neutral or unstressed state.

2. An apparatus in accordance with claim 1, wherein the transducer means includes deflection means for deflecting in response to pressure being applied to the muscle tissue and deflection sensitive means interconnected to the deflection means for sensing the amount of deflection of the deflection means and providing an electrical output signal indicative of the sense deflection.

3. An apparatus in accordance with claim 2, wherein the pressure responsive means includes amplifier means for amplifying the output signal received from the pressure sensitive means.

4. An apparatus in accordance with claim 3, further including an internal source of electrical energy whereby the apparatus need not be interconnected to an external source of energy and is portable.

5. An apparatus in accordance with claim 4, wherein the internal source of electrical energy includes a DC battery.

6. An apparatus in accordance with claim 4, wherein the first internal source of electrical energy provides electrical energy to the amplifier means and the readout means and a second source of electrical energy provides electrical energy to the supporting bridge electronics.

7. An apparatus in accordance with claim 6 wherein the first internal source of electrical energy is two DC batteries in series.

8. An apparatus in accordance with claim 1, wherein the pressure sensitive means includes an elongated bar member mounted in a housing, a first end of the bar member being fixed against movement, a second end of the bar member being free, a probe member being interconnected to the bar member proximate the free end and extending transversely of the bar member, the probe member having an end portion of constant geometry for forcing against the localized site on the patient's body.

9. An apparatus in accordance with claim 8, wherein the probe member has a cylindrical axial geometry and a contoured, curved end portion.

10. An apparatus in accordance with claim 8, wherein the probe member is hollow.

11. An apparatus in accordance with claim 10, wherein the probe member has exterior walls having a thickness which is substantially less than the axial diameter of the probe member.

12. An apparatus in accordance with claim 8, wherein the probe member is made of plastic.

13. An apparatus in accordance with claim 8, wherein the weight of the probe member is equal to or less than an amount relative to the elastic properties of the bar so as to cause an insignificant movement of the bar as the bar is moved from one orientation to another.

14. An apparatus in accordance with claim 1, wherein the transducer means includes a semiconductor strain gauge sensor cartridge suitably mounted on a bar so as to sense any deflections of the bar.

15. An apparatus in accordance with claim 1, wherein the transducer means includes a load cell device.

16. An apparatus in accordance with claim 1, further including recording means for providing a permanent record indicative of the pressure sensed by the pressure sensitive means.

17. An apparatus in accordance with claim 1, wherein the readout means comprises a digital display.

18. An apparatus in accordance with claim 1, further including a latch means for providing an output signal indicative of an operational state of the latch means, the latch means comprising means for selectively operating in one of an active operational state and an inactive operational state.

19. An apparatus in accordance with claim 18, wherein the readout means comprises:
a digital display;
means electrical interconnected to the latch means for receiving the output signal from the latch means; and
means responsive to the output signal received from the latch means for holding the digital display constant when the latch means is in an active operational state.

20. An apparatus in accordance with claim 18, further including recording means for providing a permanent record indicative of the pressure sensed by the pressure sensitive means, the recording means comprising means electrically interconnected to the latch means for receiving the output signal from the latch means, recording means further comprising means for providing a permanent record indicative of the output signal received from the latch means.

21. An apparatus in accordance with claim 1, wherein the coupling means comprises means for deriving electrical energy from alternating current voltage supply.

* * * * *